United States Patent
Collins, Sr. et al.

(10) Patent No.: US 9,921,282 B2
(45) Date of Patent: Mar. 20, 2018

(54) METHOD FOR DETERMINING FAT OR MOISTURE CONTENT

(71) Applicant: CEM Corporation, Matthews, NC (US)

(72) Inventors: Michael J. Collins, Sr., Charlotte, NC (US); Jonathan M. Collins, Charlotte, NC (US); Colin L. Simpson, Charlotte, NC (US)

(73) Assignee: CEM Corporation, Matthews, NC (US)

(*) Notice: Subject to any disclaimer, the term of this patent is extended or adjusted under 35 U.S.C. 154(b) by 1353 days.

(21) Appl. No.: 13/858,991

(22) Filed: Apr. 9, 2013

(65) Prior Publication Data

US 2013/0265051 A1 Oct. 10, 2013

Related U.S. Application Data

(60) Provisional application No. 61/622,497, filed on Apr. 10, 2012, provisional application No. 61/635,342, filed on Apr. 19, 2012.

(51) Int. Cl.
*G01N 24/08* (2006.01)
*G01R 33/44* (2006.01)
(Continued)

(52) U.S. Cl.
CPC .............. *G01R 33/44* (2013.01); *G01N 24/08* (2013.01); *G01R 33/31* (2013.01); *G01R 33/4625* (2013.01)

(58) Field of Classification Search
USPC .......... 324/300–322; 600/407–435; 436/173, 436/60, 23, 20
See application file for complete search history.

(56) References Cited

U.S. PATENT DOCUMENTS 5,049,819 A * 9/1991 Dechene ................ G01R 33/31
324/307
5,302,896 A * 4/1994 Dechene .............. G01R 33/389
324/300

(Continued)

FOREIGN PATENT DOCUMENTS

CN 101692122 A 4/2010
CN 201464391 U 5/2010

(Continued)

OTHER PUBLICATIONS

Davenel et al., Rapid moisture and fat determination by pulsed NMR for monitoring drying and coating processes of extrudates; International Journal of Food Science and Technology, 1995, vol. 30, pp. 655-657.

(Continued)

*Primary Examiner* — Melissa Koval
*Assistant Examiner* — Tiffany Fetzner
(74) *Attorney, Agent, or Firm* — Parsons Summa

(57) ABSTRACT

A method of measuring NMR response in an NMR instrument includes heating a sample at a heater temperature that is higher than the temperature of the interior of the NMR instrument, positioning the heated sample in the NMR instrument, and measuring the NMR response of the heat sample. Typically, the sample is dry and includes fat. Furthermore, a method of determining an amount of a component of a sample includes positioning a sample in an NMR instrument, applying a sequence of radio-frequency pulses to the sample, measuring the amplitudes of the signals produced by the application of the sequence of radio-frequency pulses, and determining the amount of a component in the sample using the measured amplitudes of the signals. The disclosed methods typically provide accurate (Continued)

analysis of samples in a shorter time period than traditional NMR techniques and solvent-based analysis techniques.

8 Claims, 6 Drawing Sheets

(51) Int. Cl.
  *G01R 33/31* (2006.01)
  *G01R 33/46* (2006.01)

(56) References Cited

U.S. PATENT DOCUMENTS

| | | | | |
|---|---|---|---|---|
| 5,530,350 | A * | 6/1996 | Dechene | G01R 33/389 |
| | | | | 324/307 |
| 6,218,835 | B1 | 4/2001 | Smallcombe | |
| 6,515,260 | B1 * | 2/2003 | Anderson | G01R 33/31 |
| | | | | 219/385 |
| 6,548,303 | B2 * | 4/2003 | Collins | G01N 5/04 |
| | | | | 422/68.1 |
| 6,548,304 | B2 * | 4/2003 | Collins | G01N 5/04 |
| | | | | 436/173 |
| 6,768,304 | B2 * | 7/2004 | Avizonis | G01R 33/31 |
| | | | | 324/315 |
| 6,768,305 | B1 | 7/2004 | Keifer | |
| 6,787,362 | B2 * | 9/2004 | Collins | G01N 5/04 |
| | | | | 436/173 |
| 6,972,566 | B2 | 12/2005 | Gauthausen et al. | |
| 7,002,346 | B2 | 2/2006 | Schaepman et al. | |
| 7,015,693 | B2 | 3/2006 | Corver et al. | |
| 7,125,721 | B2 * | 10/2006 | Collins | G01N 5/04 |
| | | | | 436/20 |
| 7,220,591 | B2 * | 5/2007 | Collins | G01R 33/44 |
| | | | | 436/173 |
| 7,397,241 | B2 | 7/2008 | Gauthausen et al. | |
| 8,530,239 | B2 * | 9/2013 | Collins | G01N 5/04 |
| | | | | 436/173 |
| 2002/0119575 | A1 * | 8/2002 | Collins | G01N 5/04 |
| | | | | 436/60 |
| 2002/0146833 | A1 * | 10/2002 | Collins | G01N 5/04 |
| | | | | 436/60 |
| 2002/0164806 | A1 * | 11/2002 | Collins | G01N 5/04 |
| | | | | 436/23 |
| 2002/0192707 | A1 | 12/2002 | Stockman et al. | |
| 2003/0124728 | A1 * | 7/2003 | Collins | G01N 5/04 |
| | | | | 436/20 |
| 2003/0162302 | A1 * | 8/2003 | Avizonis | G01R 33/31 |
| | | | | 324/315 |
| 2004/0214343 | A1 * | 10/2004 | Collins | G01R 33/44 |
| | | | | 436/173 |
| 2005/0222504 | A1 | 10/2005 | Otvos et al. | |
| 2006/0263900 | A1 * | 11/2006 | Collins | G01N 5/04 |
| | | | | 436/173 |
| 2013/0265051 | A1 * | 10/2013 | Collins, Sr. | G01R 33/44 |
| | | | | 324/309 |

FOREIGN PATENT DOCUMENTS

| | | |
|---|---|---|
| CN | 101770003 A | 7/2010 |
| EP | 0 605 948 A1 | 7/1994 |
| JP | H06509161 A | 10/1994 |
| JP | H08129422 A | 5/1996 |
| JP | 2004502165 A | 1/2004 |
| JP | 2005525546 A | 8/2005 |
| JP | 2007531884 A | 11/2007 |
| SU | 830 210 A1 | 5/1981 |
| WO | 92/16851 A1 | 10/1992 |
| WO | 02/01186 A1 | 1/2002 |
| WO | 2012028786 A1 | 3/2012 |

OTHER PUBLICATIONS

Annex to Form PCT/ISA/206 Communication relating to the results of the partial international search report of International Application No. PCT/US2013/035929 dated Jul. 19, 2013.

International Search Report of International Application No. PCT/2013/035929 dated Sep. 17, 2013.

Gambhir; Applications of low-resolution pulsed NMR to the determination of oil and moisture in oilseeds, Trends of Food Science & Technology, vol. 3, No. 8/9, Sep. 1992; pp. 191-196.

Leung et al., Rapid determination of total and solid fat contents in chocolate resonance; Journal of Food Science, vol. 50, No. 4, 1985, pp. 942-945.

Database WPI Week 198207, Thomson Scientific, London, AN 1982-B7897E and SU 830 201 A1 (Mosc Food Ind Inst) May 15, 1981 Abstract.

Using Nuclear Magnetic Resonance to Test Fat Content in Foods; Oxford Instruments, date unknown.

* cited by examiner

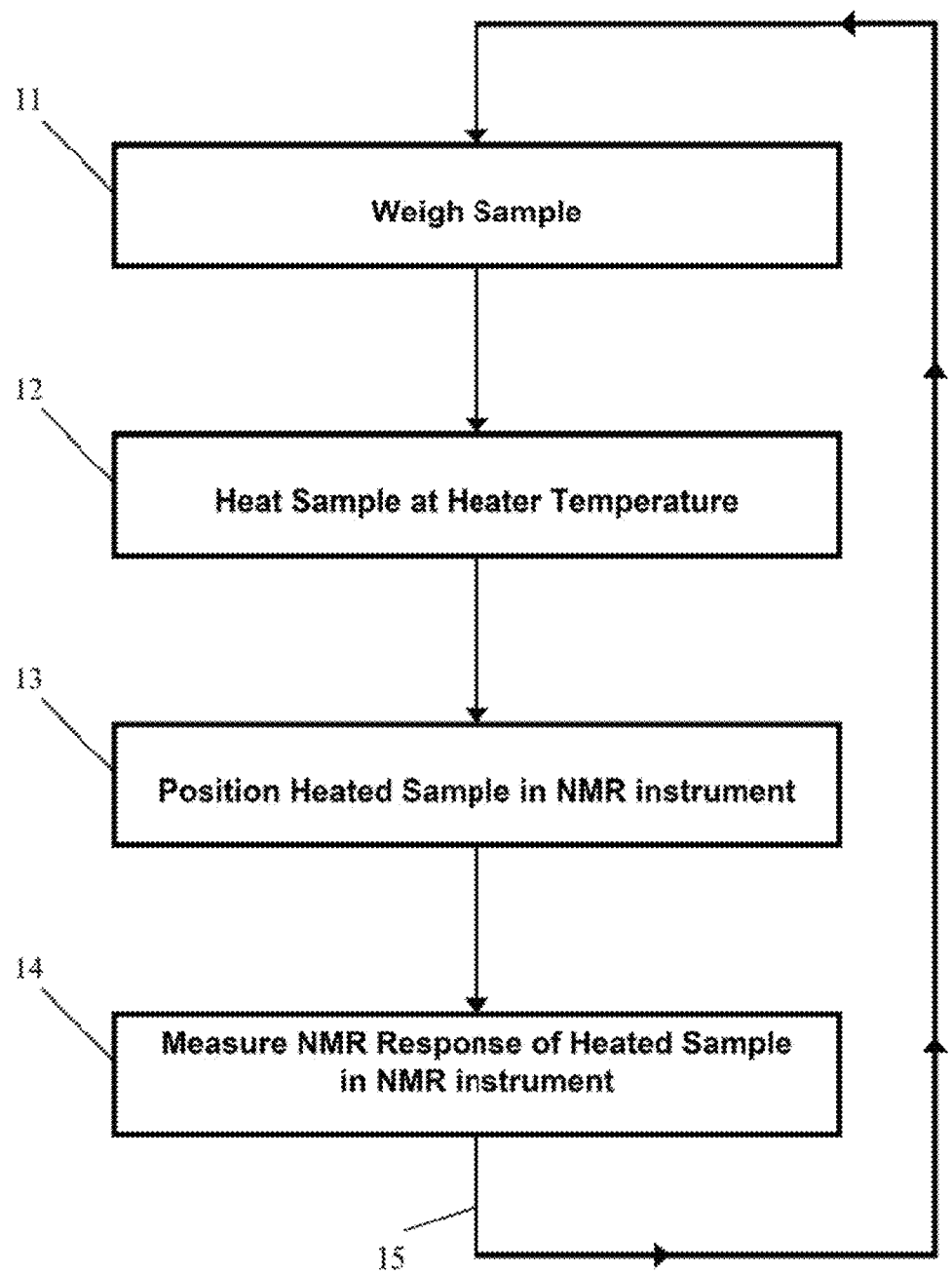

METHOD FOR DETERMINING FAT OR MOISTURE CONTENT

RELATED APPLICATIONS

This application claims priority from U.S. provisional application Ser. Nos. 61/622,497 filed Apr. 10, 2012 and 61/635,342 filed Apr. 19, 2012.

BACKGROUND

The present invention relates to techniques for determining the amount of at least one component of a sample and, more specifically, performing time-domain nuclear magnetic resonance measurements on food and related samples that are substantially dry (i.e., if they contain water, the majority of it is bound water).

Time-domain nuclear magnetic resonance measurements (time-domain NMR or TD-NMR) may be used to determine the amount of specific components in foods or animal feed. For example, the determination of fat (and oil) content in such food products can be of particular interest to commercial producers of processed food. Variation in fat and oil content during the production process can be detrimental to product quality or adversely affect production economics. The fat content of a sample also provides useful information about food products such as texture, heat resistance, mouth feel, and flavor release. Additionally, many foods are subject to various statutory and regulatory labeling and content requirements with respect to the fats and oils they contain. Information about fat and oil content is often valuable or necessary in controlling various food processing techniques.

Those skilled in the art know that the primary distinction between fats and oils is that fats are solid at room temperature and oils are liquid. Accordingly, the terms "fat" and "oil" may be used interchangeably herein.

Furthermore, variation in the moisture content of foodstuffs can be detrimental to product quality. For example, to extend the shelf life of dry products, the moisture content of the product should typically be minimized. Accordingly, information about moisture content is also valuable or necessary in controlling food processing techniques.

Traditional methods for determining the moisture and fat content of foodstuffs are time consuming and include oven drying and solvent based extractions. Therefore, the use of traditional methods for purposes of production process control is inefficient and in many cases not practical. For example, many food testing applications in high volume production plants require rapid analysis so that products may be tested before moving on to the next processing stage. Accordingly, time-consuming traditional methods are generally unacceptable. Furthermore, many methods require solvents that are expensive, often hazardous, and pose disposal challenges. Accordingly, scientists have sought alternatives for determining fat and oil content in samples.

Scientists have proposed using NMR as an alternative means of determining the fat and moisture content of foodstuffs. NMR analysis is essentially a spectroscopic method that measures a phenomenon that occurs when nuclei of certain atoms are placed in a first static magnetic field and then exposed to a second oscillating electromagnetic field. The theory and operation of NMR analysis are well understood in the art and will not be discussed in detail herein other than as necessary to describe the invention. In somewhat simplistic terms, however, during NMR analysis a substance is placed in a magnetic field that affects the "spin" of the atomic nuclei of certain isotopes of elements. The nuclei orient themselves in a specific way in response to the magnetic field. If a second radio frequency (RF) magnetic field is passed over the nuclei, the protons in the nuclei will reorient when the RF field reaches a specific frequency. When the RF field is turned off, the nuclei relax, reorient themselves again, and release energy that provides data on the molecular structure of the substance.

Under proper circumstances, NMR can distinguish not only between liquids and solids, but also between chemical compounds. Theoretically, in abstract circumstances, all protons should resonate at the same frequency or relax over the same time period. Surrounding electrons, however, interfere with the magnetic field acting upon a given proton, and thus each proton will resonate at a slightly different frequency, or relax over a different time period, depending on the electronic density around it. As a result, different compounds (and different functional groups within compounds) have different resonance frequencies and different relaxation times.

As mentioned previously, NMR has long held promise as an alternative to solvent extraction and conventional over drying for quantitatively determining the fat and moisture content of a sample. Efficiently utilizing NMR in this regard, however, has proven difficult. This difficulty is especially prevalent in determining the moisture, fat, and oil content of foodstuff samples.

For example, NMR resonance occurs over a narrow band for liquids and this narrow window of NMR resonance is used to easily distinguish liquids from solids. Traditional fat and oil analysis takes advantage of this by melting all the fat and oil in a sample prior to NMR analysis. Because many foods have a relatively high moisture content, and because high moisture content usually makes NMR analysis unfeasible, food samples typically must be thoroughly dried prior to NMR analysis.

After the sample is dried, the sample is usually heated until all the fat and oil present in the sample is assumed to have melted, with the further assumption that the only liquid remaining in the sample is fat. Such heating is typically referred to as thermal equilibration because NMR instruments typically have a set or chosen temperature of operation and samples are heated to approximately the same temperature as the NMR instrument's operating temperature. If aggressive heating techniques, such as convection ovens, microwave ovens, or high temperature heating blocks, are used to speed drying or thermal equilibration of the sample, the chemical structure of the sample may be altered (e.g., the sample may be cooked) which may alter the NMR results and provide a less accurate—or even highly inaccurate—analysis.

To this end, a variety of techniques have been employed to achieve thermal equilibration of an NMR sample. For example, a simple technique involves placing the sample in an NMR instrument and setting the interior temperature of the NMR instrument to the desired operating temperature. The sample is heated by the atmosphere within the instrument until it reaches thermal equilibration, and then the NMR measurement is performed. Although simple, this technique is very time-consuming because of the time required to achieve thermal equilibration for each sample.

U.S. Pat. No. 6,768,305 discloses a convective heating technique that requires a vertical axial bore NMR spectrometer. Such convective heating techniques often involve costs which preclude implementation of time-domain NMR instruments such as those used in the food quality control industry, because specialized NMR hardware is required which would allow flow of thermostated gases over the sample.

U.S. Pat. No. 6,218,835 discloses a method of heating a sample within an NMR instrument that includes applying a set of heating radio-frequency pulses to the sample before NMR analysis. Such RF-heating techniques involve the application of RF energy to a metal-coated sample tube to inductively heat the sample tube which then heats the sample through conductive heating. RF-heating techniques can be relatively expensive and time-consuming, and RF-heating parameters are highly sample-type dependent.

U.S. Pat. No. 7,002,346 discloses a technique that applies temperature correction factors to compensate for sample temperature differences at the NMR measurement time. The correction factors are sample-type dependent and involve relatively complicated calculations making the disclosed technique less reliable and, again, sample-type dependent.

Additionally, a variety of techniques have been employed to achieve more reliable, accurate time-domain NMR analysis. For example, U.S. Pat. No. 6,972,566 discloses a time-domain NMR technique that utilizes magnetic gradient fields to measure the fat and water content of a hydrous sample (i.e., a sample with a significant amount of free water). The magnetic gradient fields are used suppress the signal contributions from water, so that the fat and water may be measured simultaneously. The application of such magnetic gradient fields during the NMR measurement increases the complexity of the technique, the machinery required to employ the technique, and the analysis of the generated data.

U.S. Pat. No. 7,397,241 discloses another time-domain NMR technique that measures water, fat, and protein in samples. The magnetization of the sample is initially saturated using RF pulse sequences, and additional RF pulse sequences are applied to the sample while signal amplitudes are measured. The time parameters and number of RF pulses in the technique are matched to the sample. Thus, this NMR technique is sample-type dependent. Furthermore, the number of saturation and measurement sequences required makes the disclosed technique more time-consuming and complex.

Thus, there exists a need for a thermal equilibration technique that reduces (i) the risk of burning the sample, (ii) the cost of NMR equipment required to employ the technique, and (iii) the time necessary to achieve thermal equilibration. Additionally, there exists a need for a method of determining the amount of a component of a sample (e.g., a dry sample) that does not depend upon sample-particle-size and that reduces the cost of NMR equipment required to employ the technique and the time required to perform a measurement.

SUMMARY

In one aspect, the present invention embraces a method of measuring NMR response in an NMR instrument. The method includes heating a sample at a heater temperature that is higher than the temperature of the magnet of the NMR instrument for a heating period. The method then includes positioning the heated sample in an NMR instrument having an interior temperature substantially equal to the magnet temperature for a magnet period, and thereafter measuring the NMR response of the heated sample using the NMR instrument.

In an exemplary embodiment, the step of heating the sample at a heater temperature includes using conductive heating to heat the sample.

In another exemplary embodiment, the heater temperature is (i) high enough to heat the sample to a temperature approximately equal to the magnet temperature within the heating period and (ii) low enough to avoid cooking the sample within the heating period.

In yet another exemplary embodiment, the heater temperature is between about 60° C. and 80° C.

In yet another exemplary embodiment, the heating period is (i) long enough to heat the sample at the heater temperature to a temperature approximately equal to the magnet temperature and (ii) short enough to avoid cooking the sample at the heater temperature.

In yet another exemplary embodiment, the heating period is between about 30 seconds and 60 seconds.

In yet another exemplary embodiment, the magnet temperature is about 40° C.

In yet another exemplary embodiment, the magnet period is long enough for the heated sample's temperature to become approximately equal to the magnet temperature.

In yet another exemplary embodiment, the magnet period is about 60 seconds or less.

In yet another exemplary embodiment, the sample includes fat.

In yet another exemplary embodiment, the sample is dry (i.e., the sample has less than about 12 weight percent water, such as less than about 10 weight percent water, and a majority of its water is bound water).

In yet another exemplary embodiment, the method includes weighing the sample before the step of heating the sample at the heater temperature.

In yet another exemplary embodiment, the method includes heating a second sample at the heater temperature for the heating period, thereafter, positioning the second sample in the NMR instrument having an interior temperature equal to the magnet temperature for the magnet period, and thereafter, performing an NMR measurement using the NMR instrument.

In another aspect, the present invention embraces a method of determining an amount of at least one component of a sample. The method includes positioning a sample in an NMR instrument having an interior magnetic field and applying at least one sequence of first and second radio-frequency pulses to the sample using the NMR instrument. The method also includes measuring the amplitude of each first signal produced by the application of each first radio-frequency pulse to determine an FID value and measuring the amplitude of each second signal produced by the application of each second radio-frequency pulse to determine a Spin Echo value. Finally, the method includes determining the amount of at least one component of the sample by subtracting a fraction of the Spin Echo value from the FID value.

In an exemplary embodiment, the first radio-frequency pulse is a single $\pi/2$ pulse and the second radio-frequency pulse is a single $\pi$ pulse.

In another exemplary embodiment, the step of applying at least one sequence of radio-frequency pulses to the sample includes applying two or more sequences (e.g., sixteen or fewer sequences) of radio-frequency pulses to the sample. In this exemplary embodiment, the FID value is determined using the average of the measured amplitudes of the first signal, and the Spin Echo value is determined using the average of the measured amplitudes of the second signal.

In yet another exemplary embodiment, the method includes performing the steps of positioning a sample, applying radio-frequency pulses to the sample, and measuring the amplitudes of each first and second signal for multiple samples. In this exemplary embodiment, the method also includes subtracting each sample's Spin Echo value from its FID value to identify each sample's signal loss, and determining the fraction of the Spin Echo value subtracted from the FID value based on the identified signal losses.

In yet another exemplary embodiment, the fraction of the Spin Echo value subtracted from the FID value is approximately $3/22$.

In yet another exemplary embodiment, the fraction of the Spin Echo value subtracted from the FID value is approximately $1/24$.

In yet another exemplary embodiment, the sample includes fat.

In yet another exemplary embodiment, the sample is dry (i.e., the sample has less than about 12 weight percent water, such as less than about 10 weight percent water, and a majority of its water is bound water).

In yet another exemplary embodiment, the interior magnetic field is constant (e.g., static).

In yet another exemplary embodiment, the method includes weighing the sample.

In yet another exemplary embodiment, the method includes, before positioning the sample in the NMR instrument, heating the sample at a heater temperature that is higher than the temperature of the magnet of the NMR instrument for a heating period. Thereafter, the method includes positioning the heated sample in the NMR instrument, the NMR instrument having an interior temperature substantially equal to the magnet temperature and beginning the step of applying at least one sequence of radio-frequency pulses after the sample has been positioned in the NMR instrument for a magnet period.

The foregoing and other objects and advantages of the invention and the manner in which the same are accomplished will become clearer based on the followed detailed description taken in conjunction with the accompanying drawings.

BRIEF DESCRIPTION OF THE DRAWINGS

FIG. 1 depicts a flow chart of an exemplary embodiment of the method of measuring NMR response employing a thermal equilibration technique in accordance with the present invention.

DETAILED DESCRIPTION

Figure 2A:
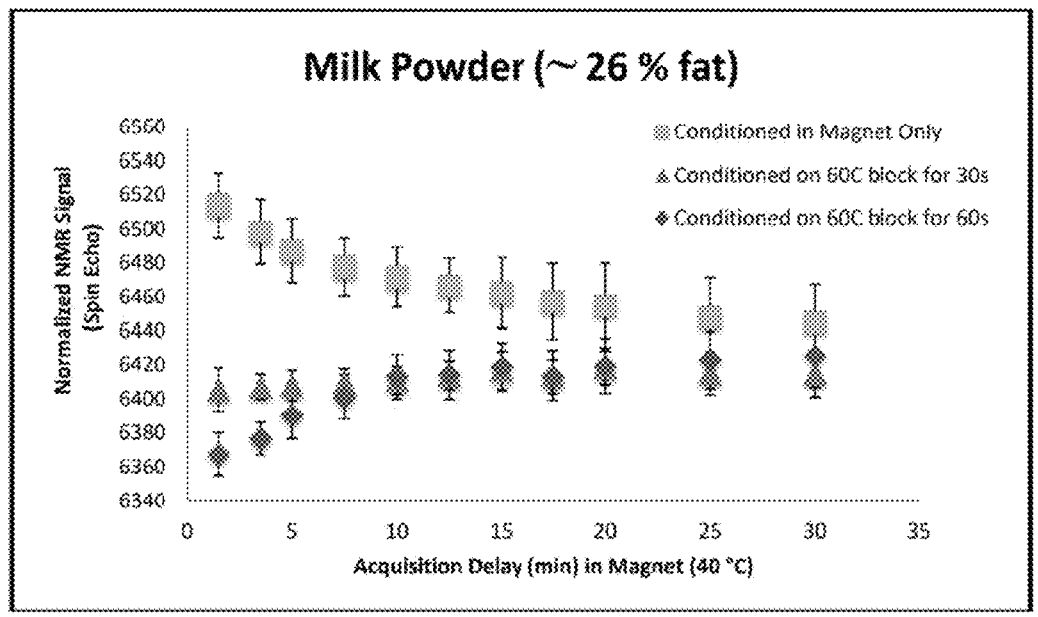
FIG. 2A graphically depicts a normalized NMR Spin Echo signal for milk powder samples as a function of acquisition delay in the NMR instrument for three different datasets used to calibrate the method of measuring NMR response employing a thermal equilibration technique in accordance with the present invention.

In one aspect, the present invention embraces a method of measuring NMR response employing a thermal equilibration technique that reduces (i) the risk of burning the sample, (ii) the cost of NMR equipment required to employ the technique, and (iii) the time necessary to achieve thermal equilibration.

FIG. 1 depicts a flow chart of an exemplary embodiment of the method of measuring NMR response employing a thermal equilibration technique in accordance with the present invention. As shown, the method includes an initial step 11 of weighing the sample. Of course, if the sample weight is known, this step 11 may not be carried out in the method.

The sample is then heated at a heater temperature in step 12. In other words, the sample is heated such that if the sample were heated until thermal equilibration was achieved, the temperature of the sample would be the heater temperature. Typically, this heater temperature is higher than the interior temperature of the NMR instrument that will be used for measuring NMR response. Generally speaking, the interior temperature of an NMR instrument is approximately equal to the temperature of the NMR instrument's magnet and is either set by the operator or preprogrammed. The magnet temperature is typically high enough to melt fats, turning them into liquids, but not so high as to burn the sample or unnecessarily weaken the signal produced during the NMR measurement. Accordingly, the magnet temperature may be 40° C.

As noted, the heater temperature of step 12 is typically higher than the interior temperature of the NMR instrument. In this regard, the heater temperature is typically high enough to heat the sample to a temperature approximately equal to the interior temperature of the NMR instrument within a heating period but low enough to avoid cooking the sample or otherwise altering its chemical composition (e.g., by causing moisture to evaporate) within the heating period. In exemplary embodiments, the heater temperature is between 60° C. and 80° C. In further exemplary embodiments, the heater temperature may depend on the weight or type of sample being tested.

Heating step 12 may include conductively heating the sample. In this regard, the sample may be placed on a heater block that is set to the heater temperature. Conductively heating the sample does not require expensive or complicated equipment.

Heating step 12 includes heating the sample at the heater temperature for a heating period. The heating period is long enough to heat the sample at the heater temperature to a temperature approximately equal to the interior temperature of the NMR instrument (e.g., the magnet temperature) and short enough to avoid cooking the sample at the heater temperature. The heating period may be between 30 seconds and 60 seconds. In exemplary embodiments, the heating period may depend on the weight or type of sample being tested. For example, longer heating periods may be used larger particle size samples due to the reduced exposed surface area of the sample.

After performing heating step 12 for the heating period, the heated sample is positioned in the NMR instrument in step 13. As noted, the NMR instrument has an interior temperature that may be approximately equal to the temperature of the NMR instrument's magnet. The sample is maintained in position in the NMR instrument for a magnet period. The magnet period is typically long enough for the heated sample's temperature to become approximately equal to the NMR instrument's interior temperature (i.e., through passive conductive heating). The magnet period is typically 60 seconds or less.

In exemplary embodiments, the sample may be transferred from one location where heating step 12 occurs to the NMR instrument. In this regard, there may be a heat loss during this transfer period. Furthermore, this transfer period and heat loss may be non-negligible. Accordingly, this transfer period is typically minimized to avoid an undesirable amount of heat loss. For example, the transfer period may be less than 5 seconds (e.g., less than 4 seconds), such as less than 3 seconds, or even less than 2 seconds.

After the magnet period, the method includes measuring the NMR response of the heated sample using the NMR instrument (i.e., step 14). In exemplary embodiments, the steps of the method can be repeated (e.g., chart line 15) for the same sample or multiple samples.

As discussed, the method of measuring NMR response employing a thermal equilibration technique includes at least the following parameters: a heating temperature, a heating period, a magnet temperature, and a magnet period. Using these parameters, the technique can be calibrated for a variety of sample types and sample particle sizes. As noted, the magnet temperature of an NMR instrument can be set by the operator or preprogrammed. Accordingly, the calibration is performed for a given magnet temperature.

Figure 2B:
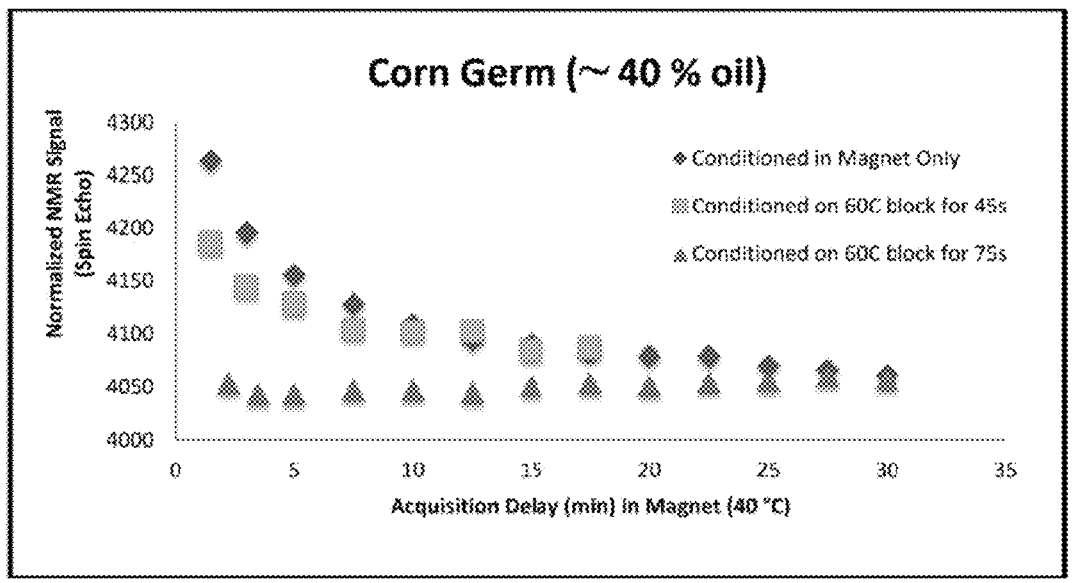
FIG. 2B graphically depicts a normalized NMR Spin Echo signal for corn germ samples as a function of acquisition delay in the NMR instrument for three different datasets used to calibrate the method of measuring NMR response employing a thermal equilibration technique in accordance with the present invention.

FIGS. 2A and 2B graphically depict weight normalized NMR Spin Echo signals for samples as a function of acquisition delay in the NMR instrument for three different datasets used to calibrate an exemplary method of measuring NMR response employing a thermal equilibration technique in accordance with the present invention. The samples used to generate the data of FIG. 2A were milk powder containing approximately 26 percent fat. The samples used to generate the data of FIG. 2B were corn germ containing approximately 40 percent oil.

In FIG. 2A, the data points identified with squares represent the NMR signal produced after placing a sample in the NMR instrument without prior heating (i.e., without performing step 12). The data points identified with triangles represent the NMR signal produced after performing the prior heating step 12 at a heater temperature of 60° C. for a heating period of 30 seconds. The data points identified with diamonds represent the NMR signal produced after performing step 12 at a heater temperature of 60° C. for a heating period of 60 seconds. Finally, the x-axis of FIG. 2A is equivalent to the magnet period.

In FIG. 2B, the data points identified with diamonds represent the NMR signal produced after placing a sample in the NMR instrument without prior heating (i.e., without performing step 12). The data points identified with squares represent the NMR signal produced after performing step 12 at a heater temperature of 60° C. for a heating period of 45 seconds. The data points identified with triangles represent the NMR signal produced after performing step 12 at a heater temperature of 60° C. for a heating period of 75 seconds. Finally, the x-axis of FIG. 2B is equivalent to the magnet period.

Using the data of FIGS. 2A and 2B for a given magnet temperature, appropriate heating temperatures, heating periods, and magnet periods can be identified to achieve approximately the same NMR response as if the sample had been placed in the NMR instrument without prior heating but with a reduced time-to-measurement. For example, FIG. 2B shows that heating a sample of corn germ at a heater temperature of 60° C. for a heating period of 75 seconds, placing the heated sample in the NMR instrument for a magnet period of approximately 2 minutes, and thereafter measuring the NMR response yields an equivalent NMR signal as if the sample had been placed in the NMR instrument for 30 minutes. Thus, this exemplary method achieves an NMR measurement in approximately one-tenth of the time of a conventional method employing conventional thermal equilibration.

In exemplary embodiments, the step 14 of measuring the NMR response of the heated sample using the NMR instrument is performed for a measurement period that is less than 30 seconds (e.g., less than 20 seconds, such as about 15 seconds or less). Such short measurement periods assure that the sample temperature does not change significantly during the NMR measurement step, thereby ensuring consistent results of the NMR analysis. Furthermore, if the same measurement period is repeated for similar samples, accurate results can be assured.

Typically, the present methods are performed on samples having a moisture content of less than 10-12 weight percent. Furthermore, the samples typically contain primarily bound water as opposed to free water. In this regard, the samples may be dry in nature (e.g., potato-based chip samples or milk powders) or may be dried (e.g., semi-moist animal feeds) using a variety of drying techniques (e.g., microwave drying). Generally speaking, dry samples (i.e., samples containing primarily bound water) are more readily suitable for NMR analysis because bound water's movement is more restricted during NMR measurement than that of free water. That said, it is within the scope of the present invention to perform the present methods on wet samples, albeit wet samples having relatively low amounts of free water. Alternatively, the present methods may include an initial or intermediate step of drying the sample before conducting NMR analysis.

In another aspect, the present invention embraces a method of determining the amount of a component of a sample (e.g., a dry sample) that is not sample-particle-size dependent and that reduces the cost of NMR equipment required to employ the technique and the time required to perform a measurement.

Typically, the method of the present invention uses a time-domain NMR technique. In time-domain NMR techniques, a sample is placed in a magnetic field and radio-frequency pulses are applied to the sample. After a radio-frequency pulse is applied, the relaxation of the nuclei is converted to a signal (e.g., a current induced by the relaxation in coils surrounding the sample) that is measured. The amplitude of the measured signal and its decay rate provide information about the sample's contents.

Figure 3:
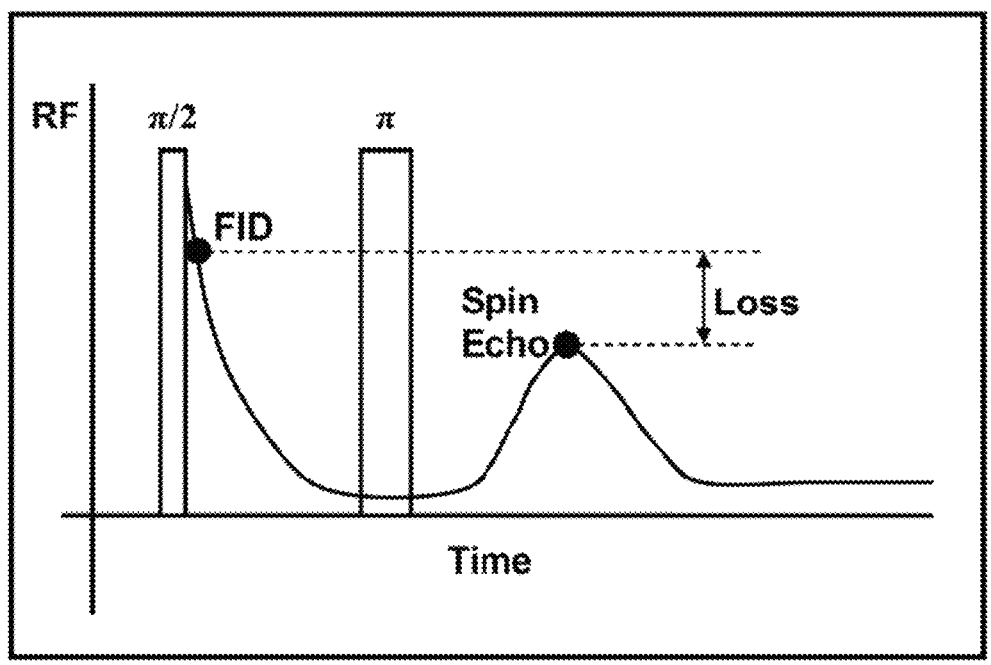
FIG. 3 graphically depicts an exemplary sequence of radio-frequency pulses and NMR response signals utilized in the method of determining an amount of at least one component of a sample in accordance with the present invention.

FIG. 3 graphically depicts an exemplary sequence of radio-frequency pulses and NMR response signals utilized in the method of determining an amount of at least one component of a sample in accordance with the present invention. A magnetic field is applied to the sample and the sequence of radio-frequency pulses are applied. As shown, an initial π/2 pulse (or 90° pulse) is applied and flips the magnetic moment of the spins of the nuclei into a plane that is perpendicular to the magnetic field. The spin moments then precess, and a decaying signal is produced (See FIG. 3). The amplitude of the decaying signal can be measured and is generally referred to as the Free Induction Decay or FID.

After a period of time, a π pulse (or 180° pulse) is applied that reverses the direction of the precessing spin moments. As faster precessing spin moments converge with the orientation of slower precessing spin moments, a second increasing and then decaying signal can be measured, and the amplitude of this signal is generally referred to as the Spin Echo. This sequence of a π/2 pulse followed by a π pulse is sometimes referred to as a Hahn echo sequence. Typically, the time period between the initial π/2 pulse and the subsequent π pulse is less than the time that the FID signal would take to fully decay. In other words, the π pulse is applied before the FID signal has completed decayed. This time period between the initial π/2 pulse and the subsequent π pulse is typically long enough that the spin's of the nuclei of the sample's bound moisture no longer have a net magnetic moment.

Additional information regarding this time-domain NMR technique is disclosed in commonly-assigned U.S. Pat. No. 6,548,303, which is hereby incorporated by reference in its entirety. Generally speaking, the FID and Spin Echo, both individually and in combination, provide information regarding the chemical composition of a sample (e.g., its fat and/or moisture content).

Figure 4:
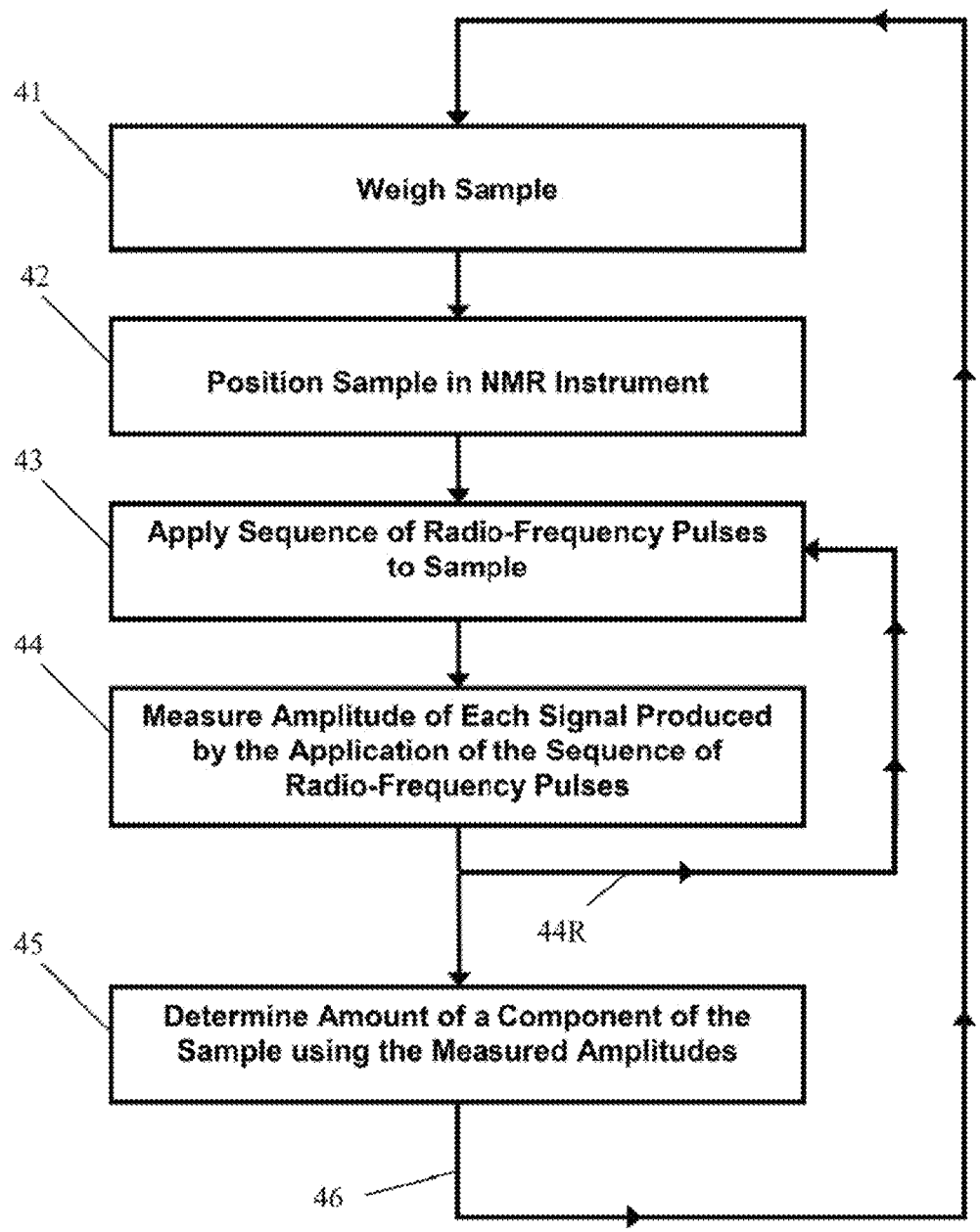
FIG. 4 depicts a flow chart of an exemplary embodiment of the method of determining an amount of at least one component of a sample in accordance with the present invention.

FIG. 4 depicts a flow chart of an exemplary embodiment of the method of determining an amount of at least one component of a sample in accordance with the present invention. As shown, the method includes an initial step 41 of weighing the sample. Of course, if the sample weight is known, this step 41 may not be carried out in the method.

The method includes a step 42 of positioning the sample in an NMR instrument. Suitable NMR instruments are available from several sources including CEM Corporation of Matthews, N.C. and Oxford Instruments of Tubney Woods, Abingdon, Oxfordshire, UK. The NMR instrument has an interior magnetic field. Typically, the interior magnetic field is constant (i.e., static) but may also be a gradient magnetic field.

The method also includes a step 43 of applying a sequence of radio-frequency pulses to the sample using the NMR instrument. The sequence of radio-frequency pulses typically includes a first radio-frequency pulse and a second radio-frequency pulse. In exemplary embodiments, the sequence is a Hahn echo sequence. Accordingly, the first radio-frequency pulse is a single π/2 pulse, and the second radio-frequency pulse is a single π pulse.

The amplitude of each signal produced by the application of the sequence of radio-frequency pulses is measured in step 44. In this regard, the amplitude of the first signal produced by the application of the first radio-frequency pulse may be used to determine an FID value (See FIG. 3). The amplitude of the second signal produced by the application of the second radio-frequency pulse may be used to determine a Spin Echo value (See FIG. 3).

In exemplary embodiments, two or more sequences of radio-frequency pulses are applied to the sample and the signals produced by each application of radio-frequency pulses are measured. In other words, steps 43 and 44 of FIG. 4 may be repeated as indicated by the line 44R. Typically, sixteen or fewer sequences of radio-frequency pulses are applied to the sample to limit the duration of the NMR measurement. That said, it is within the scope of the present invention to apply more than sixteen sequences of radio-frequency pulses to the sample (e.g., thirty or more). Generally speaking, increasing the number of applied sequences and signal measurements can improve the accuracy of the measurement. If multiple sequences of radio-frequency pulses are applied to the sample, the FID value may be determined using the average of the measured amplitudes of the first signal, and the Spin Echo value may be determined using the average of the measured amplitudes of the second signal.

The method includes a step 45 of determining an amount of a component of the sample using the measured amplitudes. Theoretically, the FID value corresponds to the amount of every component within the sample that produces an NMR signal. That said, practical limitations on the speed at which the FID can be measured typically result in the loss of signals from solid components (e.g., proteins and carbohydrates) in the sample. Thus, the practical measured FID value corresponds to the amount of moisture and fat in the sample (i.e., the liquid components in the sample). As noted, the method is typically performed on a dry sample that is substantially free from free water. Accordingly, the FID value typically corresponds to the amount of bound moisture and fat in the sample.

The Spin Echo value theoretically corresponds to the amount of free water and fat in the sample because the bound water signal typically dissipates very quickly. Again, assuming a dry sample that is substantially free from free water, the Spin Echo value corresponds to the amount of fat in the sample.

Thus, assuming that the sample is dry, the Spin Echo value can theoretically be subtracted from the FID value to yield the moisture content (e.g., the bound moisture content) of the sample. Without being bound to any particular theory, however, the present inventors have found that, in practice, a percentage of the signal generated by the fat in the sample is lost between the initial π/2 pulse and subsequent π pulse (See FIG. 3, Loss). Furthermore, the percentage of lost fat signal is dependent on the percentage of fat and type of fat (e.g., animal fat vs. plant fat) within the sample.

Accordingly, the step 45 of determining an amount of a component of the sample is typically performed by subtracting a fraction of the Spin Echo value from the FID value (e.g., to yield a converted FID value). The fraction of the Spin Echo value may be determined by performing steps 42, 43, and 44 for multiple samples (e.g., multiple different sample types having different particle sizes), subtracting each sample's Spin Echo value from its FID value to identify each sample's signal loss, and determining the fraction of the Spin Echo value subtracted from the FID value based on the identified signal losses. The fraction of the Spin Echo value subtracted from the FID value may be approximately $3/22$ (e.g., for samples of dairy powders and other powders). In exemplary embodiments, the fraction of the Spin Echo value subtracted from the FID value may be approximately $1/24$ (e.g., for samples of larger particle size, such as chips).

The fraction of the Spin Echo value subtracted from the FID value may also be dependent on the sample type. For example, the fraction of Spin Echo value subtracted from the FID value may be different for a baked food product sample as compared to a similar non-baked food product sample. Typically, baked samples have lower moisture and/or fat content and may, therefore, necessitate a different fraction of Spin Echo value to be subtracted from the FID value.

In exemplary embodiments, the method includes determining the amount of moisture in a sample. In such exemplary embodiments, the moisture content of the sample is determined by subtracting a fraction of the Spin Echo value from the FID value and then subtracting the entire Spin Echo value from this difference. Stated differently, the moisture content of the sample is determined by subtracting (i) the Spin Echo value and (ii) a fraction of the Spin Echo value from the FID value.

Furthermore, the fraction of the Spin Echo value subtracted from the FID value may be determined by analyzing a given sample set using conventional long-chemistry techniques and analyzing the same sample set using an NMR measurement technique. In this exemplary embodiment, the fraction of the Spin Echo value subtracted from the FID value may be considered a correction factor that matches the curves of the results of the conventional long-chemistry analysis and the results of the NMR measurement analysis for the sample set. For example, the results of an analysis and determination of a correction factor for different types of chip samples is demonstrated in the following tables and FIGS. 5-6.

Table 1 provides data for a variety of chip samples obtained using a method that does not employ a correction factor as used in exemplary embodiments according to the present invention (i.e., a comparative or conventional method). For each sample, the table provides the reference moisture (i.e., the known moisture content of the sample), the FID value (FID), the Spin Echo value (S.E.), and the theoretical moisture in the sample based on the NMR measurement (i.e., FID–S.E.=Moisture).

TABLE 1

| Sample | Reference Moisture | FID | S.E. | Moisture |
|---|---|---|---|---|
| 1 | 1.46 | 2763.04 | 2512.57 | 250.47 |
| 2 | 1.82 | 3901.57 | 3594.32 | 307.25 |
| 3 | 1.98 | 3815.69 | 3505.25 | 310.44 |
| 4 | 0.27 | 3745.31 | 3499.91 | 245.4 |

Figure 5:
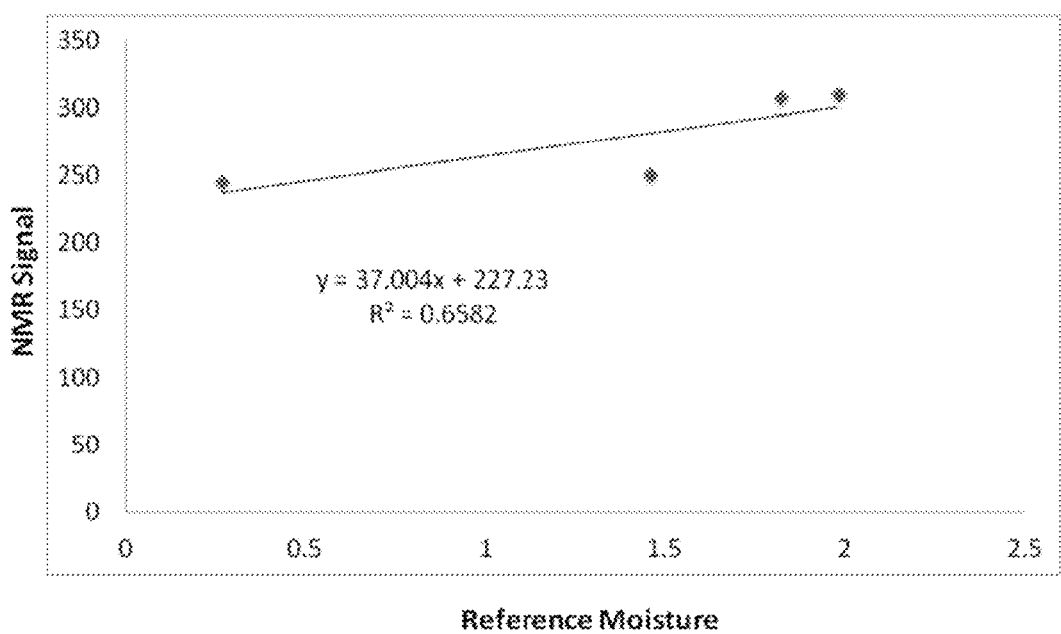
FIG. 5 plots NMR measured moisture as a function of reference moisture for four samples as obtained using a comparative method of NMR analysis.

FIG. 5 plots the data of Table 1. The NMR-measured moisture (i.e., Moisture in Table 1) is plotted as a function of Reference Moisture for each sample. A linear trendline for the data is also depicted. As shown, the trendline represents a relatively poor correlation between the Reference Moisture value and the moisture measured with the comparative NMR method.

Table 2 provides data for chip samples 1-4 obtained using an exemplary method that employs a correction factor of 1/24. For each sample, the table provides the reference moisture (i.e., the known moisture content of the sample), the FID value (FID), the Spin Echo value (S.E.), the corrected FID value ($FID_{corr}$), and the corrected moisture in the sample based on the NMR measurement (i.e., $FID_{corr}$–S.E.=$Moisture_{corr}$).

TABLE 2

| Sample | Reference Moisture | FID | S.E. | $FID_{corr}$ | $Moisture_{corr}$ |
|---|---|---|---|---|---|
| 1 | 1.46 | 2763.04 | 2512.57 | 2658.35 | 145.78 |
| 2 | 1.82 | 3901.57 | 3594.32 | 3751.81 | 157.49 |
| 3 | 1.98 | 3815.69 | 3505.25 | 3669.64 | 164.39 |
| 4 | 0.27 | 3745.31 | 3499.91 | 3599.48 | 99.57 |

Figure 6:
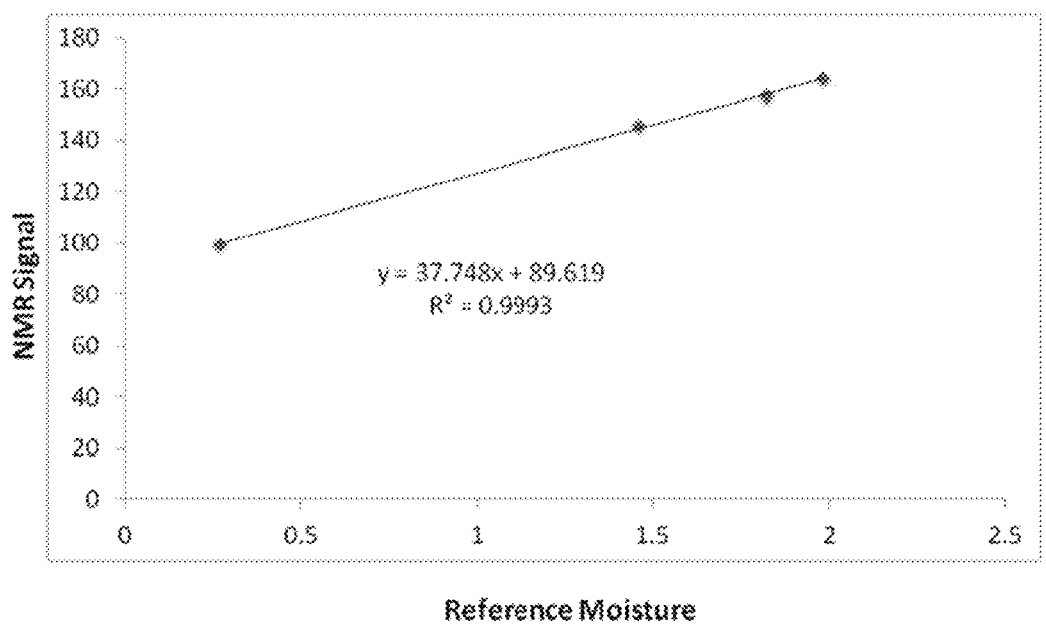
FIG. 6 plots NMR measured moisture as a function of reference moisture for four samples as obtained using an exemplary method of NMR analysis.

FIG. 6 plots the data of Table 2. The corrected NMR-measured moisture (i.e., $Moisture_{corr}$ in Table 2) is plotted as a function of Reference Moisture for each sample. Again, a linear trendline for the data is depicted. As shown, the trendline represents a very good correlation between the Reference Moisture value and the corrected NMR-measured moisture (i.e., $Moisture_{corr}$). Thus, Tables 1-2 and FIGS. 5-6 demonstrate the improved accuracy of this exemplary method.

Exemplary embodiments of the present inventive methods (i.e., the method of measuring NMR response employing a thermal equilibration technique and the method of determining the amount of a component of a sample) do not include a step of weighing the sample or samples upon which they are performed. In this regard, exemplary embodiments may correlate a measured FID value with a sample weight. The appropriate correlation factors for weight-determination for a given sample type may be determined by comparing measured FID values with a variety of samples of known weight.

Alternatively, exemplary methods that do not weigh the sample or samples may include a step of preparing a given, fixed, volume of the sample and then correlating a measured FID value with sample weight. For example, the sample or samples may be prepared using a fixed volume measurement device, such as a measuring scoop or spoon. Preparing a given, fixed, volume of the sample limits the range of expected weights assuming packing densities for various sample types remains fairly constant. Accordingly, an FID calibration curve may be obtained using known weights and samples using a fixed volume measurement device, and the curve could be used to presume the weight of subsequent samples. Such a method of predicting sample weight using fixed sample volumes and a measured FID value is particularly effective across a broad range of high fat dairy powders (e.g., various infant formula types and brands) and full cream milk powders.

Exemplary embodiments of the method of determining an amount of at least one component of a sample have been described as determining the amount of moisture in the sample. As will be understood by those of ordinary skill in the art, the methods described herein may also be used to determine the amount of fat within a given sample.

Furthermore, the exemplary embodiments have been described as employing a technique of subtracting a fraction of the Spin Echo value from the FID value. The methods described herein are not so limited, and, in exemplary embodiments, may employ a technique of adding a fraction of the Spin Echo value to the Spin Echo value to obtain a corrected Spin Echo value. The corrected Spin Echo value may then be subtracted from the measured FID value.

In exemplary embodiments, the method of determining an amount of at least one component of a sample may include aspects of the thermal equilibration technique. In this regard, before the step 42 of positioning the sample in the NMR instrument, the sample is heated at a heater temperature that is higher than the temperature of the magnet of the NMR instrument for a heating period. Thereafter, the step 42 of positioning the heated sample in the NMR instrument is performed, and the NMR instrument has an interior temperature substantially equal to the magnet temperature. Step 43 of applying a sequence of radio-frequency pulses to the sample is begun after the sample has been positioned in the NMR instrument for a magnet period.

In exemplary embodiments, the step 45 of determining an amount of component of the sample can be performed by a processing unit programmed to perform the determination in accordance with the present invention. For example, a typical PC, if programmed appropriately, has the necessary computing power to perform the determining step 45. In this regard, the NMR data of the sample may be fed to the processing unit where it may be mathematically manipulated using calculations to quantitatively determine the quantity of fat and oil in the sample. Typically, calculations are based on the sample type (e.g., entered by the operator) and comparative NMR data for the same or similar sample types. The use of known NMR response data from known samples is generally most appropriate for analyses in which samples of the same material are tested for quality control or other similar purposes. Stated differently, and using foodstuffs as the example, samples of a particular meat product will almost always have a moisture/fat/oil/protein content that falls within an expected profile. As a result, the number of applied sequences of radio-frequency pulses may be very reasonable.

In some exemplary embodiments, the various steps of the methods of the present invention may be automated by accessory components to the NMR instrument. In this regard, the automated components may be controlled by a processing unit to perform each step at precise times. For example, an automated component may weigh the sample (e.g., by placing it on an electronic scale), place the sample on a heating block and remove the sample after a precise heating period, then position the heated sample in the NMR instrument. Such automation improves the precision of the analysis and reduces the activity required from a technician. Appropriate robotics and their controls are well understood in this art and appropriate items can be selected and incorporated with the invention without undue experimentation.

Additionally, the methods of the present invention may including placing the sample on a pliable sample pad, rolling or folding the sample pad around the sample to surround the sample, placing the rolled or folded sample pad and sample into a sheet material that is wrapped around the sample and sample pad during NMR analysis (e.g., a sheet material in an open-ended, tubular shape). Typically, the sample pad and sheet material are free of atoms that would provide a chemical shift that would interfere with or mask the chemical shift of the protons in the sample. Such sample pads facilitate the prevention of significant, unwanted, moisture loss during heating steps performed before NMR analysis.

In the specification and/or figures, typical embodiments of the invention have been disclosed. The present invention is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The invention claimed is:

1. A method of measuring an NMR response of a dry sample with an NMR instrument having an NMR magnet, comprising:

conductively heating the dry sample so that it is substantially free from free water moisture on a heater block for a defined heating period, at a heater temperature that is higher than the temperature of the magnet of the NMR instrument, up to a temperature that is (i) high enough to heat the dry sample to a temperature greater than the magnet temperature of the NMR instrument within the defined heating period and (ii) low enough to avoid cooking the dry sample within that same defined heating period;

thereafter, positioning the heated sample inside the NMR instrument, where the NMR instrument has an interior temperature substantially equal to the magnet temperature, and then keeping the heated sample inside the NMR instrument over a magnet period, where the magnet period is the time period that is long enough for the dry sample's heated temperature to become approximately equal to the magnet temperature of the NMR instrument; and thereafter, measuring the NMR response of the dry heated sample, within the NMR instrument, by using the NMR instrument; and providing the measurement of the NMR response of the dry sample as an output of the NMR instrument that may be recorded, plotted, graphed or displayed.

2. The method according to claim 1, wherein the heater temperature is a temperature between and including 60° C. and 80° C.

3. The method according to claim 1, wherein the heating period is a duration of time from 30 seconds through 60 seconds.

4. The method according to claim 1, wherein the magnet temperature is 40° C.

5. The method according to claim 1, wherein the magnet period is 60 seconds or less.

6. The method according to claim 1, wherein the dry sample comprises fat.

7. The method according to claim 1, comprising, before the step of heating the sample on the heater block for the defined heating period at the heater temperature, weighing the dry sample by placing the dry sample on an electronic scale.

8. The method according to claim 1, comprising:
repeating the performing of the method of measuring an NMR response of a dry sample with an NMR instrument having an NMR magnet, as set forth in claim 1, with a second dry sample that is also substantially free from free water moisture; and
after performing the method of claim 1 with the second dry sample, providing the measurement of the NMR response of the second dry sample as an additional output of the NMR instrument that may also be recorded, plotted, graphed or displayed.

* * * * *